United States Patent [19]

Babson et al.

[11] Patent Number: 5,149,501
[45] Date of Patent: Sep. 22, 1992

[54] MULTICHAMBERED CONTAINER AND INSTRUMENT FOR PERFORMING DIAGNOSTIC TESTS

[75] Inventors: Arthur L. Babson, Chester; Thomas Palmieri, Paramus, both of N.J.; Douglas R. Olson, Doylestown, Pa.

[73] Assignee: Cirrus Diagnostics, Inc., Chester, N.J.

[21] Appl. No.: 471,416

[22] Filed: Jan. 29, 1990

[51] Int. Cl.⁵ .............................. G01N 31/02
[52] U.S. Cl. .................................. 422/58; 422/61; 422/64; 422/72; 422/102; 436/45; 436/808; 436/809; 435/287; 435/288; 435/975; 494/10
[58] Field of Search .............. 436/45, 808, 807; 422/101, 64, 58, 72, 61, 102, 100; 494/10; 435/287–288, 296–298, 975

[56] References Cited

U.S. PATENT DOCUMENTS

| | | |
|---|---|---|
| 3,565,582 | 2/1971 | Young ........................ 436/45 |
| 3,586,484 | 6/1971 | Anderson . |
| 4,030,834 | 6/1977 | Bauer et al. . |
| 4,148,607 | 4/1979 | Bernoco et al. ........... 494/10 |
| 4,187,979 | 2/1980 | Cullis et al. . |
| 4,225,558 | 9/1980 | Peterson et al. . |
| 4,244,513 | 1/1981 | Fayer et al. ............... 494/10 |
| 4,482,342 | 11/1984 | Lueptow et al. . |
| 4,521,519 | 6/1985 | Draeger et al. ........... 436/174 |
| 4,636,360 | 1/1987 | Sakurada et al. .......... 422/64 |
| 4,705,630 | 11/1984 | Gordon et al. . |
| 4,746,← | 11/←88 | Kerscher et al. .......... 436/175 |
| ←,←,← | 9/1988 | Ichikawa et al. .......... 422/101 |
| 4,849,177 | 7/1989 | Jordan ....................... 422/64 |
| 4,865,813 | 9/1989 | Leon .......................... 422/58 X |
| 4,876,206 | 10/1989 | Guigan ....................... 436/45 |
| 4,877,746 | 10/1989 | Jansson et al. ........... 435/7.7 |
| 4,933,147 | 6/1990 | Hollar et al. .............. 436/45 X |
| 5,011,663 | 4/1991 | Innocenti .................. 422/72 X |
| 5,035,861 | 7/1991 | Grandone .................. 422/72 X |

Primary Examiner—Robert J. Hill, Jr.
Attorney, Agent, or Firm—Whitham & Marhoefer

[57] ABSTRACT

An instrument (50) automatically determines the concentrations of HDL cholesterol, LDL cholesterol, total cholesterol and triglycerides for a sample (80) of whole, anticoagulated blood placed in a doughnut shaped container (10). The sample (80) is first separated into its blood cell and plasma (84) constituents using high speed centrifugation (54) and a thixotropic gel (82). Part of the plasma (84) is then deposited in an HDL separation chamber (14) where LDL cholesterol and VLDL cholesterol are precipitated by a reagent and the precipitant is sedimented by high speed centrifugation (54) against V-shaped grooves (40) in the outermost wall (38) of the HDL separation chamber (14). Part of the plasma (84) is diluted ten-fold. The supernatant in the HDL separation chamber is then placed in a cuvette reaction chamber (b 18) where it reacts with a cholesterol reagent. The diluted plasma is placed in two other cuvette reaction chambers (18) where it reacts with chloesterol and triglycerides reagents, respectively. Calibration reagents, stored in storage chambers (20), react in two other cuvette reaction chambers (18) to establish a reference absorbance. A pipettor (58) handles all the fluid transfers in the doughnut shaped container (10) and operates in conjunction with a slow speed motor (56) that precisely moves the spindle (52) on which the doughnut shaped container (10) is mounted. A colorimetric measuring system (70, 72, and 74) monitors the absorbance of chemical reactions occurring in the cuvette chambers (18).

47 Claims, 2 Drawing Sheets

MULTICHAMBERED CONTAINER AND INSTRUMENT FOR PERFORMING DIAGNOSTIC TESTS

BACKGROUND OF THE INVENTION

1. Field of the Invention

The subject invention is directed to a device for automatically performing a series of diagnostic tests on an anticoagulated whole blood sample of a patient. More specifically, the total cholesterol, low density lipoprotein (LDL) cholesterol, high density lipoprotein (HDL) cholesterol, and triglycerides concentrations in the blood plasma are automatically determined and used in assessing the patient's risk of developing coronary artery disease.

2. Description of the Prior Art

Cholesterol plays an essential role in the body in building cell membranes, in regulating sex hormones, and in aiding digestion. Cholesterol is produced in the liver and transported to cells via the bloodstream, but it may also be obtained directly from fatty foods typically found in western diets. The LDL carrier particles carry 60-80% of the blood's total cholesterol. An excess of LDL carrier particles may lead to plaque build up on the interior walls of a patient's coronary arteries. Blockage of the artery causes angina (chest pain) and, over time, large build ups can lead to heart attacks. The condition of having plaque on the artery walls is referred to as atherosclerosis. The HDL carrier particles remove excess cholesterol from the blood and tissue cells and may collect cholesterol from plaque, thus reversing the process of "narrowing" the artery. In regard to the risk placed on the heart, HDL cholesterol has been called "good" cholesterol and LDL cholesterol has been called "bad" cholesterol. Triglycerides or triacylglycerols are lipids which are a major nonprotein organic component of blood plasma. Triglycerides are typically referred to as "fats" and are a major fuel source for human beings. High levels of triglycerides are typically found in obese persons and are indicative of undue stress being placed on the heart.

In the medical profession, it is a common practice to test for total cholesterol, HDL cholesterol, LDL cholesterol, and triglycerides in order to determine the cardiac risk profile of a patient. Generally, a doctor will obtain three or four separate samples of blood from the patient and send them to a laboratory for conducting the tests. After the test results are returned to the doctor, the doctor and patient can discuss treatment if necessary, such as a change of diet or the prescription of drugs.

Sending out blood samples for testing is not the best solution for determining the cardiac risk profile of a patient. Ideally, it would be advantageous for a doctor to have the testing performed in house such that the possibility of a mix up is avoided and so that the doctor becomes aware of the test results more quickly. However, most doctor's offices are not sufficiently staffed to perform the necessary tests in house. Consequently, an automated instrument which performs the tests for the doctor would greatly improve upon the prior art procedure.

SUMMARY OF THE INVENTION

It is therefore an object of this invention to provide an instrument capable of automatically performing a variety of diagnostic tests on a single whole blood sample.

It is another object of the invention to provide a disposable container having a plurality of chambers wherein the chambers are used for storing reagents, performing tests, and executing separations.

According to the invention, a doughnut shaped container having a plurality of chambers is used in conjunction with an instrument having a pipettor and a colorimetric light detecting system. The doughnut shaped container fits on a spindle which is capable of rotating at slow speeds for positioning a particular chamber underneath the pipettor and is capable of rotating at high speeds for performing separations by high speed centrifugation. The colorimetric light detecting system comprises a light source and reference detector positioned in a hub on which the spindle rotates and a photodetector positioned in the instrument chassis. Some of the chambers in the doughnut shaped container have optical windows which allow making colorimetric measurements of reactions taking place within the chambers. Other chambers in the doughnut shaped container include gel used in the high speed centrifugal separation of blood cells from plasma, precipitating reagents for separating HDL cholesterol from very low density lipoprotein (VLDL) and LDL cholesterol, reagents for performing diagnostic tests to determine HDL cholesterol, total cholesterol, and triglyceride concentrations, a calibrating solution having a known concentration of total cholesterol and triglycerides (glycerol) for providing a measurement reference, and water for flushing the pipette, performing dilutions, and balancing the doughnut shaped container during high speed rotation. To access a chamber, the pipettor, which translates on the Z-axis, must penetrate through a rubber coated plastic membrane formed over openings in a lid welded to the doughnut shaped container. The instrument operates according to the directions of a computer program which schedules the time periods for high speed centrifugation, for low speed chamber alignment, and for control of the pipettor.

Before testing the sample, the whole blood must first be separated into its blood cell and plasma constituents. An aliquot of the patient's whole, anticoagulated blood is transferred to the blood separation chamber. The blood separation chamber contains a thixotropic gel positioned against the outermost side wall of the chamber. Positioning the gel against the outermost side wall can be accomplished by high speed centrifugation. During a high speed centrifugation, blood cells diffuse through the gel towards the outermost side wall of the chamber while the plasma remains in the volume between the innermost side wall and the thixotropic gel. For example, after a 20,000 r.p.m. rotation for 20 seconds to a minute, the blood cells are packed against the narrower, outermost wall of the blood separation chamber, the thixotropic gel is positioned against the packed blood cells, and the plasma remains as a free liquid pooled near the innermost wall of the blood separation chamber. The narrowness of the blood separation chamber at its outermost end helps hold the thixotropic gel in its lined up configuration after rotation of the doughnut shaped container is halted. The plasma is retrieved from the blood separation chamber with the pipettor by translating it into the blood separation chamber near its innermost end and withdrawing the plasma. The sloped bottom the blood separation chamber promotes pooling of the plasma such that maximum retrieval is possible.

Before conducting tests on the plasma for total cholesterol and triglycerides, LDL and VLDL cholesterol are separated from a portion of the plasma for determining the HDL cholesterol concentration. The doughnut shaped container is rotated to position an HDL cholesterol separation chamber underneath the pipettor and a volume of plasma equal to the volume of LDL/VLDL cholesterol precipitating reagent present in the HDL cholesterol separation chamber is dispensed. The plasma remaining in the pipettor is then dispensed into a storage chamber and a ten fold dilution of the plasma is prepared After the plasma and the LDL/VLDL cholesterol precipitating reagent have mixed for a short period of time, the doughnut shaped container is again spun at high speed to precipitate the LDL and VLDL cholesterol out of solution. The HDL cholesterol separation chamber has vertical grooves in its outermost sidewall for holding the LDL/VLDL cholesterol precipitate. The high speed spin packs the LDL/VLDL cholesterol precipitate into the grooves such that the precipitate is firmly held there against when the doughnut shaped container is stopped, thereby preventing remixing the precipitate with the supernatant solution which contains the HDL cholesterol.

As stated above, a ten-fold dilution of the plasma is prepared in a storage chamber. The ten-fold dilution is used in the determination of total cholesterol and triglycerides concentration in the plasma. The dilution has been selected to be ten-fold to promote more accurate pipetting, whereby greater accuracy is achieved when pipetting a larger volume. The degree of dilution can be varied to suit the needs of the operator. The ten-fold dilution can be made by dispensing a known amount of plasma into a fixed quantity of water in the storage chamber and then discarding the rest of the plasma in the pipettor into a waste chamber or by dispensing all of the plasma in the pipettor into an empty storage chamber and then appropriately diluting the plasma with water retrieved from a water filled chamber.

After the HDL cholesterol separation, a variety of diagnostic tests are performed. The doughnut shaped container has five cuvette chambers in which chemical reactions take place. The cuvette chambers have optical windows of sufficient clarity to allow colorimetric measurements to be made therethrough. Preferably, the cuvette chambers are integrally formed with the disposable, plastic, doughnut shaped container. Each cuvette chamber is filled with a known amount of reagent for performing a particular test. In a preferred arrangement, three of the cuvette chambers contain a known amount of a cholesterol specific reagent and two of the cuvette chambers contain a known amount of a triglyceride specific reagent. A storage chamber in the doughnut shaped container contains a calibrating solution having a known concentration of cholesterol and a known concentration of triglycerides (glycerol). The calibrating solution is dispensed in two of the cuvette chambers, one with the cholesterol specific reagent and another with the triglyceride specific reagent, such that absorbance measurements for known concentrations of cholesterol and triglycerides can be compared with the absorbance measurements obtained for the plasma sample. It is anticipated that the doughnut shaped container could be used for other colorimetric tests on the separated plasma such as detecting albumin, glucose, lactate dehydrogenase, or any other constituent present in plasma. If other tests were to be performed, suitable reagents would be provided in the cuvette chambers and suitable calibrating solutions would be provided in the storage chambers. It should also be noted that the doughnut shaped container could include additional cuvette and storage chambers such that more than three constituents could be tested for. The doughnut shaped container includes several storage chambers filled with wash water such that the pipettor can be cleaned between each retrieval and dispensing operation.

A "blank" absorbance measurement is taken of each cuvette chamber before any diagnostic tests are performed. The "blank" absorbance measurements are calibrated against a water reference present in a sixth cuvette chamber. In operation, an aliquot of the HDL supernate is pipetted into a cholesterol specific reagent containing cuvette and aliquots of the ten-fold dilution of plasma are pipetted into a cholesterol specific reagent containing cuvette and a triglyceride specific reagent containing cuvette, respectively. The pipette needle is rinsed with wash water between dispensing the HDL supernate and the ten-fold diluted plasma. During the washing step, the outside of the pipette is "squeegeed" by the rubber coated plastic membrane adhered over the wash chamber, thereby removing sample solution from the outside of the pipettor in addition to rinsing the inside. Aliquots of the cholesterol and triglyceride (glycerol) calibrating solution are pipetted into cholesterol specific reagent and triglyceride specific reagent containing cuvettes, respectively, with a washing step being performed between each pipetting step.

The triglyceride specific reagent is preferably a two part liquid solution which is mixed before transferring the ten-fold diluted plasma sample or the calibrating solution to their respective cuvette chambers. The triglyceride specific reagent is preferably a combination of enzymes which conclude in a peroxidase reaction that is ultimately what is measured. The triglyceride specific reagent is made by combining one part of the reagent from a storage chamber with the other part that is positioned within the cuvette chamber before the ten-fold diluted plasma sample or the calibrating solution is added. After combining the two parts and before adding the ten-fold diluted plasma sample or the calibrating solution, the absorbance is measured to establish a "blank" measurement. Alternatively, the triglyceride specific reagent can be prepared from a tablet positioned within the cuvette chamber. Water from a water filled chamber is added by pipette to the cuvette chamber to form a liquid triglyceride specific reagent just prior to the chemical reaction. The disadvantage of the tablet method for creating the triglyceride specific reagent is that the tablet tends to be very hygroscopic, thereby imposing a very dry packaging requirement.

The concentration of a chemical constituent in the blood plasma is determined from the colorimetric measurements of the cuvette chambers. A first method of concentration determination comprises allowing enough time for the reactions taking place in the cuvette chambers to all go to completion, then colorimetrically measuring each of the reaction chambers, and then subtracting the "blank" measurement from the final measurement such that the concentration can be calculated from the difference. Ten minutes should be a sufficient time period for allowing the cholesterol specific and triglycerides specific reactions to reach completion. A second method of concentration determination comprises periodically monitoring the reactions in each of the cuvette chambers while the reactions are taking place and predicting the expected absorbance at the reaction endpoint such that the concentration can be computed from the difference between the predicted absorbance for the endpoint and the "blank" measurement. Periodic monitoring of the reactions is achieved by having the computer controller direct the stepper motor to rotate each of the cuvette reaction chambers to a position between the light source and the light detector while the reactions take place. The second method has a speed advantage over the first method in that the time needed for predicting an endpoint should be shorter than simply letting the reactions go to completion. A simple example of the second method is to determine that the endpoint of a reaction has been achieved whenever two consecutive absorbance measurements yield the same result. It is anticipated that other methods of predicting the absorbance at the reaction endpoint which utilize computer analysis of the absorbance measurements with respect to time can be employed.

In the preferred embodiment, the concentrations of HDL cholesterol, total cholesterol, and triglycerides are determined. The concentrations are determined from the absorbance measurements resulting from reactions of the HDL supernate and ten-fold diluted plasma samples with the cholesterol specific and triglycerides specific reagents relative to the absorbance measurements resulting from reactions of the calibrating solution with the cholesterol specific and triglycerides specific reagents. As discussed above, other constituents present in plasma such as glucose, lactate dehydrogenase (LD/LD-1), albumin, alkaline phosphatase, amylase, bilirubin, urea ((blood/urea/nitrogen) or (BUN)), calcium, creatinine, aspartate aminotransferase (GOT), hemoglobin, phosphorous, total protein, and uric acid can be determined according to a similar procedure. The concentration of VLDL cholesterol is calculated by dividing the determined triglycerides concentration by five. The concentration of LDL cholesterol is calculated by subtracting the determined HDL cholesterol concentration and the calculated VLDL cholesterol concentration from the determined total cholesterol concentration. The patient's concentration values for total cholesterol, HDL cholesterol, LDL cholesterol, and triglycerides are provided on a computer printout or display to the operator. An interpretation of the data could be provided with the printout.

BRIEF DESCRIPTION OF THE DRAWINGS

The foregoing and other objects, aspects and advantages of the invention will be better understood from the following detailed description of the preferred embodiments of the invention with reference to the accompanying drawings, in which.

BRIEF DESCRIPTION OF THE PREFERRED EMBODIMENT OF THE INVENTION

Figure 1:
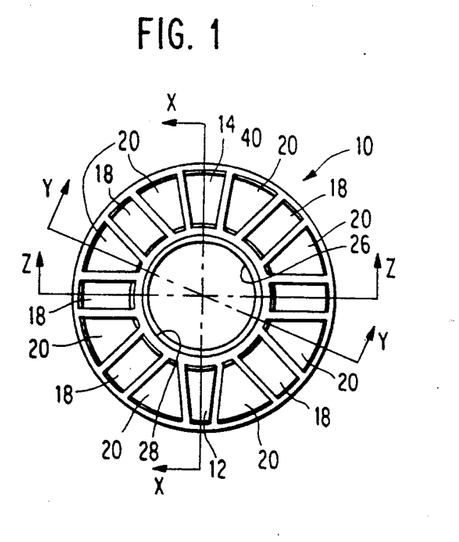
FIG. 1 is a plan view of the disposable, doughnut shaped container showing the plurality of chambers in which the separations and diagnostic tests are performed.
Figure 2:
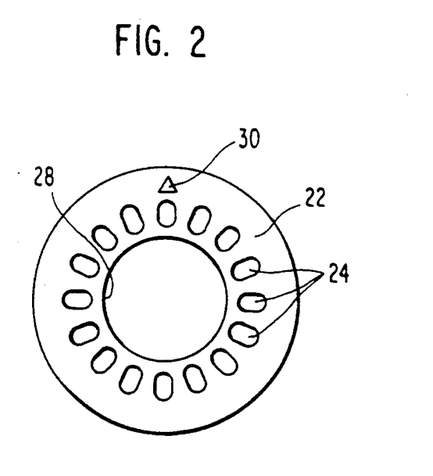
FIG. 2 is a plan view of a lid which is ultrasonically welded to the top of the doughnut shaped container shown in FIG. 1.
Figure 3:
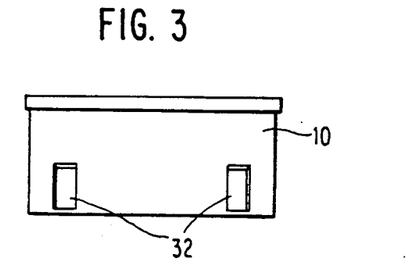
FIG. 3 is a side view of the doughnut shaped container of FIG. 1 showing outside window sections for two of the cuvette chambers in the doughnut shaped container.

Referring now to the drawings and, more particularly to FIGS. 1–3, a doughnut shaped container 10 includes a whole blood separation chamber 12, an HDL cholesterol separation chamber 14, six cuvette reaction chambers 18, and eight storage or dilution chambers 20. A lid 22 having sixteen openings 24 is ultrasonically welded to the doughnut shaped container 10 such that the openings 24 provide access to the various chambers 12, 14, 18, and 20. After the lid 22 is affixed to the doughnut shaped container, each chamber 12, 14, 18, and 20 is pressure tested to assure no leaks are present. Pressure testing assures that none of the materials, discussed in detail below, which are prepackaged in the chambers 12, 14, 18, and 20 will leak out during a high speed spin. The inside diameter 26 of the doughnut shaped container 10 fits on a spindle (not shown) for high speed rotation. A locking nub 28 secures the doughnut shaped container 10 to the spindle and alignment indicia 30 aids in installing the doughnut shaped container 10 properly. The cuvette reaction chambers 18 each have windows 32 (shown only on the exterior in FIG. 3 but also present on the interior diameter 26 as shown in FIGS. 4a and 4c) that are of sufficient optical quality to allow colorimetric measurements of chemical reactions occurring within the chambers 18 to be made therethrough.

Figure 4A:
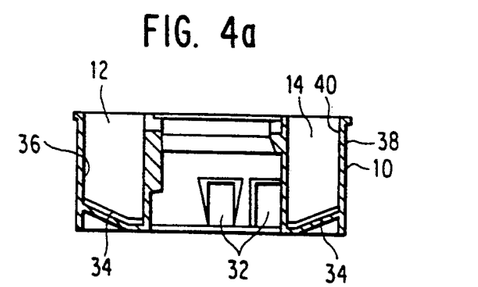
FIGS. 4a–c are cross-sectional side views of the doughnut shaped container shown in FIG. 1 showing the whole blood and HDL separation chambers, water or reagent filled storage chambers, and the cuvette reaction chambers, respectively.
Figure 4B:
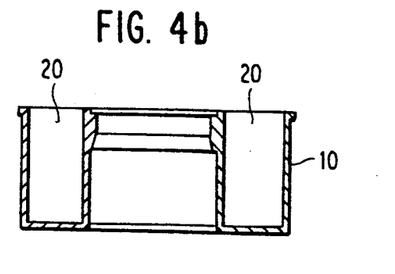
Figure 4C:
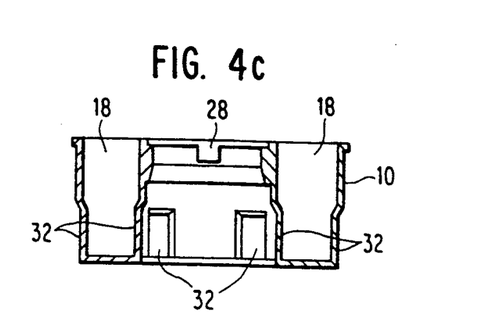
Figure 5:
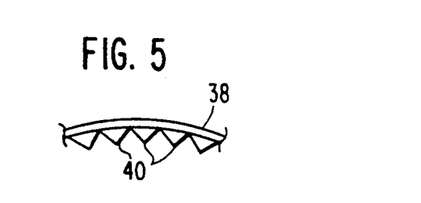
FIG. 5 is an exploded top view of the outermost wall of the HDL separation chamber shown in the doughnut shaped container of FIG. 1.

FIGS. 4a–c show cross-sectional side views of the doughnut shaped container 10. Both the blood separation chamber 12 and the HDL separation chamber 14 have sloping bottom walls 34 which are designed to pool a mixture therein such that a maximum amount of the mixture can be retrieved with a pipettor (in the case of blood separation chamber the mixture retrieved is plasma and in the case of the HDL separation chamber the mixture retrieved is plasma without LDL or VLDL cholesterol). The sloping bottom walls 34 also aid in moving constituents against the outermost walls 36 and 38, respectively, during a high speed spin. As best shown in FIG. 5, the outermost wall 38 of the HDL separation chamber 14 has vertical V-shaped grooves 40. The V-shaped grooves 40 aid in holding a precipitate on the outermost wall 38, that is packed thereagainst during a high speed spin, after the doughnut shaped container 10 has stopped rotating such that the precipitate does not re-mix with the supernatant. The storage containers 20, shown in FIG. 4b, have a box like cross-section, while the cuvette reaction chambers 18, shown in FIG. 4c, have integrally formed window sections 32. The window sections 32 are of sufficient optical clarity to allow colorimetric measurements to be made therethrough.

Figure 6:
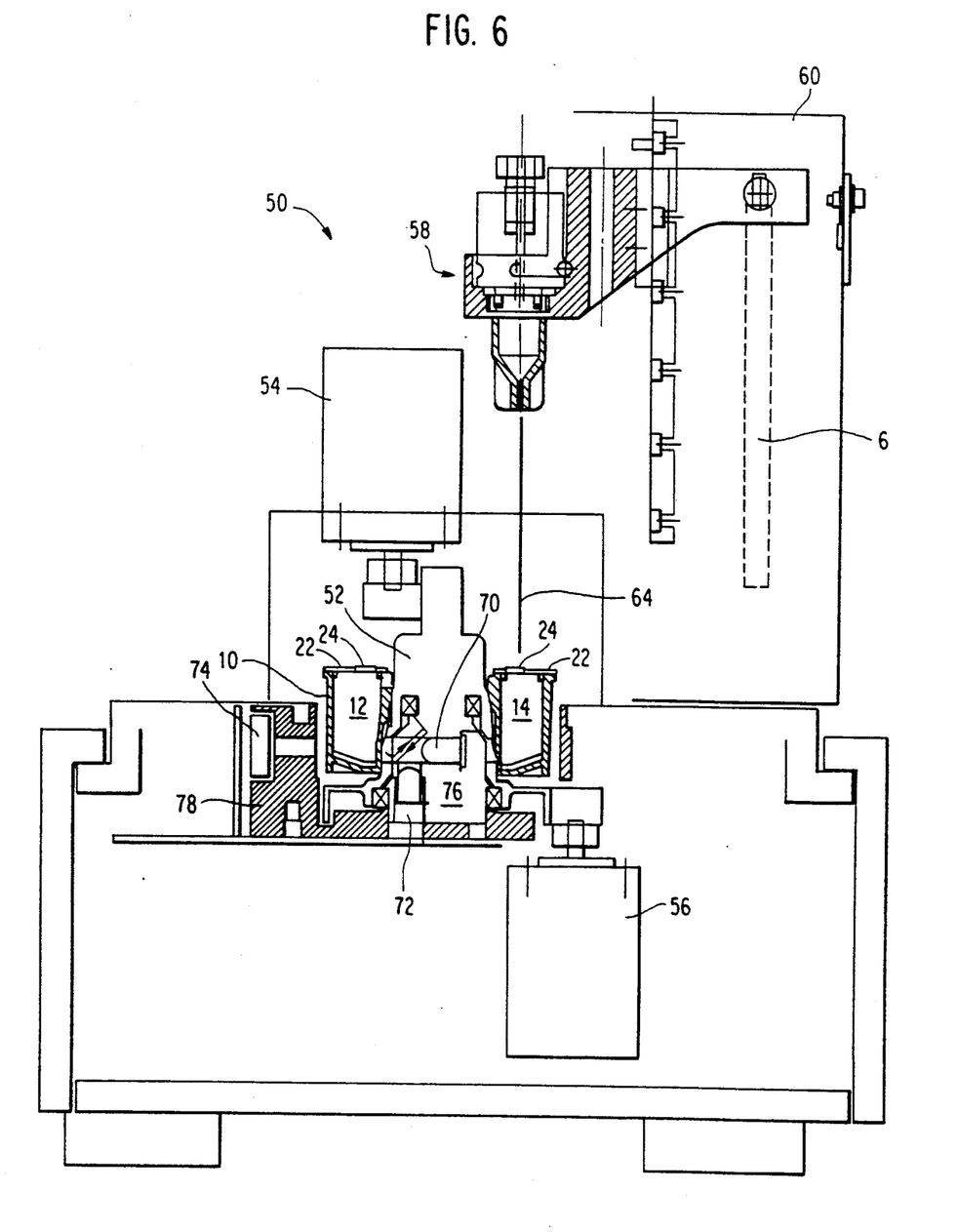
FIG. 6 is a side view, partially in section, showing details of the doughnut shaped container positioned on the spindle of the automatic cardiac risk profile instrument.

FIG. 6 shows the instrument 50 in which the doughnut shaped container 10 is utilized. The doughnut shaped container 10 is fitted onto a spindle 52 which is alternatively rotatable by a high speed spinning motor 54 or a low speed stepper motor 56. The high speed spinning motor 54 is capable of rotating the spindle 52 in excess of 20,000 r.p.m. for achieving the separation of plasma from blood cells during the whole blood separation and for sedimenting the VLDL and LDL cholesterol precipitate against the V-shaped grooves 40 in the HDL separation chamber 18 during the HDL separation. The low speed stepper motor 56 is capable of accurately positioning each of the chambers 12, 14, 18, and 20, underneath the pipettor 58. A single motor capable of rotating the spindle 52 at very high speeds and also being capable of accurately positioning the doughnut shaped container 10, as described above, could be substituted for the high and low speed motors 54 and 56, respectively.

The pipettor 58 is mounted on a frame 60 and is translatable on the Z-axis within a guide 62. Up and down movement of the pipettor 58 can be achieved with a stepper motor or by other means well known in the art. A length of teflon tubing (not shown) connects the pipettor 58 to an air displacement pump (not shown) controlled by a stepper motor (not shown) which controls the suction and dispensing operations of the pipettor 58. Other techniques for controlling the suction and dispensing operations, which are well known in the art, could also be used. The pipettor needle 64 is positioned to pass through the openings 24 in the lid 22 of the doughnut shaped container 10. The doughnut shaped container 10 is prepackaged with the gel, precipitating reagents, calibrating solution, diagnostic reagents, and water in the appropriate chambers 12, 14, 18, and 20. A rubber coated plastic membrane (not shown) is adhered over the openings 24 such that access to the chambers 12, 14, 18, and 20 is accomplished by the pipettor needle 64 breaking through the rubber coated plastic membrane and penetrating into the chamber 12, 14, 18 or 20. The rubber coating acts like a squeegee when the pipettor needle 64 is withdrawn from the chamber 12, 14, 18, or 20 by wiping off the outside surface of the needle 64.

The instrument 50 includes a colorimetric measuring system for monitoring the reactions which occur in the cuvette reaction chambers 18 of the doughnut shaped container 10, and a computer (not shown) for analyzing data from the colorimetric measuring system. The colorimetric measuring system comprises an light source 70, a reference photodetector 72, and a measurement photodetector 74. The light source 70 is selected in accordance with the wavelengths at which the chemicals being tested for absorb energy. For example, an LED which emits light in the green region is suitable for detecting the cholesterol and triglyceride specific reaction absorbances. It is anticipated that a tungsten lamp together with a color filter wheel could be used as the light source 70. The light source 70 and the reference photodetector 72 are fixedly positioned within the hub 76 on which the spindle 52 rotates. The measurement photodetector 74 is positioned within the instrument chassis 78 at a fixed position from the light source 70. Colorimetric measurements are made through the windows 32 (shown in FIGS. 3, 4a, and 4c) in the cuvette reaction chambers 18. When a measurement is to be made, the doughnut shaped container 10 is rotated to position the cuvette reaction chamber 18 between the light source 70 and the measurement photodetector 74. Reference photodetector 72 aids in adjusting the emission of light from light source 70.

A computer controller (not shown) controls the operations of the high speed motor 54, the low speed stepper motor 56, the pipettor 58, and the colorimetric measuring system 70, 72, and 74. By controlling the positioning of the doughnut shaped container 10 with the low speed stepper motor 56, the pipettor 58 is used to transfer sample and calibrating solutions to appropriate cuvette reaction chambers 18 and to perform washing operations in water filled storage containers 20. By controlling the high speed centrifuging in the doughnut shaped container 10 with the high speed motor, the plasma can be separated from the blood cells in the whole blood separation chamber 12 and the LDL and VLDL precipitate can be sedimented from the plasma solution containing HDL cholesterol in the HDL separation chamber 14. By controlling the timing of the low speed stepper motor 56 and the colorimetric measuring system 70, 72, and 74, colorimetric measurements of each of the reaction chambers 18 can be periodically made while the chemical reactions occur.

In operation, a sample of whole blood is placed in the whole blood separation chamber 12, the doughnut shaped container 10 is then placed on spindle 52 of instrument 50, and diagnostic tests for blood plasma constituents are automatically conducted according to a computer controlled schedule. A key advantage of this invention is the doughnut shaped container 10 being prepackaged with the gel, precipitating reagents, calibrating solution, diagnostic reagents, and water. Separation of the plasma from the blood cell components, followed by a chemical analysis being automatically performed on the plasma in another chamber in the same container distinguishes this invention from the prior art. As discussed below, the concentration of any plasma constituent such as cholesterol, triglycerides, glucose, lactate dehydrogenase (LD/LD-1), albumin, alkaline phosphatase, amylase, bilirubin, urea ((blood-/urea/nitrogen) or (BUN)), calcium, creatinine, aspartate aminotransferase (GOT), hemoglobin, phosphorous, total protein, uric acid, et cetera, can be determined with the appropriate selection of light sources, reagents, and calibrating solutions.

Figure 7A:
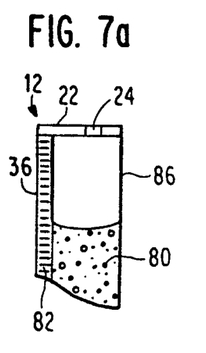
FIGS. 7a–b are cross-sectional side views of the whole blood separation chamber showing, respectively, the whole blood sample with the thixotropic gel and the blood cells separated from the plasma by the thixotropic gel.
Figure 7B:
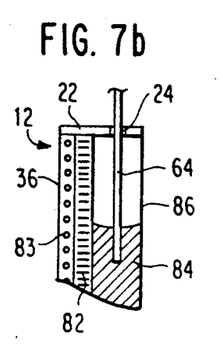

Referring now to FIGS. 1, 4a, 6, 7a, and 7b, the first operation performed is the separation of plasma from blood cells FIG. 7a shows a 200 μsample of a patient's whole, anticoagulated blood 80 is pipetted into the whole blood separation chamber 12 of the doughnut shaped container 10. The blood separation chamber 12 includes a thixotropic gel 82, used in the separation procedure, which is packed against the outermost wall 36 of the blood separation chamber 12, by high speed centrifugation or other suitable techniques, before the blood 80 is added. A suitable thixotropic gel 82 may be the gel from SST tubes manufactured by Becton Dickinson of New Jersey, Sure Sep ® available from Organon Technika of North Carolina, or any other suitable gel. The doughnut shaped container is placed on spindle 52 of instrument 50 and rotated by the high speed motor 54 at a speed of 20,000 to 23,000 r.p.m. for a suitable period of time, which may be twenty seconds to a minute. After the high speed spin, the blood cells 83 and the thixotropic gel 82 line up on the outermost wall 36 of the whole blood separation chamber 12 and the plasma 84 remains as a free liquid positioned towards the innermost wall 86 of whole blood separation chamber 12. The blood cells 83 are separated from the plasma 84 by the blood cells 83 diffusing through the thixotropic gel 82 during the high speed spin. The thixotropic gel 82 and the blood cells 83 are held against the outermost wall 36 of the whole blood separation chamber 12 due to the thixotropic nature and the specific gravity of the gel 82. The narrowness of the whole blood separation chamber 12 towards its outermost wall 36 aids in holding the thixotropic gel 82 in its lined up position after the spinning has stopped. The sloped bottom 34 of the whole blood separation chamber 12 aids in allowing the plasma 84 to pool in the volume between the thixotropic gel 82 and the innermost wall 86 such that maximum retrieval with the pipettor 64 is realized. In addition, the sloped bottom 34 aids in moving the blood cells 83 up the outermost sidewall 36. After the high speed spin, the low speed stepper motor 56 moves the doughnut shaped container 10 to a position where the pipettor 58 is positioned above the whole blood separation chamber 12. As best shown in FIG. 7b, the pipettor needle 64 translates through opening 24 in lid 22 to retrieve the separated plasma 84. The pipettor needle 64 enters the whole blood separation chamber 12 at a position closer to the innermost wall 86 so that only the plasma 84 is retrieved.

Referring now to FIGS. 1, 4a, 4b, 5, and 6 the next operations performed are the separation of HDL cholesterol from LDL and VLDL cholesterol and the dilution of a plasma 84 sample. The doughnut shaped container 10 is rotated by the low speed stepper motor 56 to position the HDL cholesterol separation chamber 14 underneath pipettor 58. A volume of plasma 84, equal to a volume of the LDL/VLDL cholesterol precipitating reagent present within the HDL cholesterol separation chamber 14, is dispensed by the pipettor 58 into the HDL cholesterol separation chamber 14 (the pipette needle 64 must break through the rubber coated plastic membrane adhered over the opening 24 in lid 22 before dispensing the plasma 84). The LDL/VLDL cholesterol precipitating reagent can be phosphotungstic acid reagent available from Data Medical Associates of Texas. The plasma 84 and the LDL/VLDL cholesterol precipitating reagent are allowed to mix for a short period of time and the doughnut shaped container 10 is then spun at high speed to separate the LDL/VLDL cholesterol precipitate from the supernatant solution, where the supernatant solution contains plasma having HDL cholesterol. As best shown in FIG. 5, the outermost wall 38 has vertical V-shaped grooves 40 for holding the packed LDL/VLDL cholesterol precipitate thereagainst after the high speed spin has stopped; thereby, preventing the LDL/VLDL cholesterol precipitate from re-mixing with the HDL cholesterol in the supernatant. After the high speed spin, HDL cholesterol can be tested by retrieving a volume of the supernatant from the HDL cholesterol separation chamber with the pipettor 58.

As described above, the ten-fold dilution of the plasma 84 sample is used to achieve more accurate results via more accurate pipetting of sample volumes. The concentration of the cholesterol and triglyceride calibrating solution used is consistent with this dilution. The doughnut shaped container 10 is rotated to position a storage chamber 20 underneath the pipettor 58. Preferably, the storage chamber 20 is initially empty, and the plasma 84 remaining in the pipette needle 64 is dispensed in the storage chamber 20. An appropriate volume of water from a water filled storage container 20 is then retrieved and dispensed into the storage container 20 with the plasma 84 to achieve the ten-fold dilution. Alternatively, a fixed volume of plasma 84 in the pipettor needle 64 is dispensed into a storage chamber 20 having a fixed volume of water therein. The remaining plasma 84 is discarded by dispensing into a waste storage chamber 20. The pipette needle 64 is washed between each dispensing procedure using water from a water filled storage chamber 20. The ten-fold dilution can be made before or after the high speed spin for separating the HDL cholesterol.

Unlike the cholesterol reagent, which can be an enzymatic liquid reagent available from Stanbio Laboratories of Texas that is present in three of the cuvette chambers 18 of the doughnut shaped container 10, the triglycerides reagent is a two part reagent. In a preferred embodiment, the triglycerides reagent, which is used in two of the cuvette reaction chambers 18 of the doughnut shaped container 10, is a two liquid reagent available from Stanbio Laboratories where one reagent is positioned within one of the storage chambers 20 and the other reagent is present within the cuvette chamber 18. Just prior to conducting the triglycerides test, the pipettor 58 is used to combined the two reagents within the cuvette chamber 18. In an alternative embodiment, the triglycerides reagent can be created from a tablet available from EM diagnostic systems of New Jersey. The tablet would be present within the cuvette chamber 18 and would be diluted with water from a water filled storage container 20 using the pipettor 58 just prior to testing.

Referring now to FIGS. 1 and 6, after the HDL cholesterol separation, the ten-fold dilution, and the creation of the triglycerides reagent in two of the cuvette chambers 18, five chemical reactions are started sequentially and run simultaneously in five of the six cuvette chambers 18. Before any of the chemical reactions are started, a "blank" absorbance measurement for each cuvette chamber 18 is made using the colorimetric measuring system 70, 72, and 74. One of the cuvette chambers 18 is a water "blank" used for calibrating the colorimetric measuring system 70, 72, and 74. The remaining five cuvette chambers 18 contain the cholesterol and triglycerides specific reagents. After the "blank" measurement, the following five reactions are simultaneously conducted in the five cuvette chambers 18:

(1) An aliquot of the supernatant from the HDL cholesterol separation chamber 14 is pipetted into a first cuvette chamber 18 containing a cholesterol specific reagent.

(2) An aliquot of ten-fold diluted plasma from the storage chamber 20 is pipetted into a second cuvette chamber 18 containing the cholesterol specific reagent.

(3) An aliquot of ten-fold diluted plasma from the storage chamber 20 is pipetted into a third cuvette chamber 18 containing a triglyceride specific reagent.

(4) An aliquot of a calibrating solution containing a known concentration of cholesterol is pipetted from a first reagent storage chamber 20 into a fourth cuvette chamber 18 containing the cholesterol specific reagent. A suitable cholesterol calibrating reagent is available from the New England Reagent Laboratory of Rhode Island.

(5) An aliquot of the calibrating solution, which also contains a known concentration of glycerol, is pipetted into a fifth cuvette chamber 18 containing the triglyceride specific reagent. Note that it is easiest to combine the glycerol and cholesterol in a single calibrating solution which can be used for either calibrating measurement (due to enzymatic specificity); however, it is also possible to use two separate calibrating solutions.

The pipette needle 64 is washed in a clean water filled storage container 20 between each transfer of fluid into the respective cuvette chambers 18. As described above, the rubber coated plastic membrane adhered over the opening 24 in the lid 22 aids in "squeegeeing" clean the exterior of the pipette needle 64 as it is withdrawn from a water filled chamber 20.

The concentration of a chemical constituent in the blood plasma 84 is determined from the colorimetric measurements of the cuvette chambers 18.

In a first method for determining concentration, the doughnut shaped container 10 is permitted to incubate for a time sufficient for all five of the chemical reactions to proceed to completion. Ten minutes is believed to be suitable for the cholesterol specific and triglycerides specific reagents to fully react with either the plasma sample or the calibrating solution. The doughnut shaped container 10 is then rotated under the control of stepper motor 56 to position each of the cuvette chambers 18 between the light source 70 and the measurement detector 74 and a colorimetric measurement is made. A computer (not shown), which utilizes signals output from the colorimetric measuring system 70, 72, and 74, subtracts the "blank" absorbance measured before the reactions occurred from the "final" absorbance measured after the reaction period. The difference between the "blank" and the "final" absorbance is then used to calculate the concentration of the constituent.

In a second method for determining concentration, each of the cuvette chambers 18 are periodically measured colorimetrically and the "expected" absorbance for the reaction endpoint is predicted. Periodic monitoring is achieved by having the stepper motor 56 rotating the doughnut shaped container 10 to position each of the cuvette chambers 18, one after another while the reactions are occurring, between the light source 70 and the measurement detector 74 and colorimetrically measuring the reaction. The second method has a speed advantage over the first method in that the time needed for predicting an "expected" absorbance at the endpoint is shorter than simply letting the reactions go to completion. Similar to that discussed above, a computer (not shown), which utilizes signals input from the colorimetric measuring system 70, 72, and 74, subtracts the "blank" absorbance measured before the reactions occurred from the predicted "expected" absorbance for the reaction endpoint. The difference between the "blank" and the "expected" absorbance is then used to calculate the concentration of the constituent. A simple example of the second method is to determine that the endpoint of a reaction has been achieved whenever two consecutive absorbance measurements yield the same result, i.e., the absorbance measurement which is twice consecutively measured is the "expected" absorbance at the endpoint. It is anticipated that other methods of predicting the absorbance at the reaction endpoint which utilize computer analysis of the absorbance measurements with respect to time can be employed.

In the preferred embodiment, the concentrations of HDL cholesterol, total cholesterol, and triglycerides are determined. The concentrations are determined from the absorbance measurements resulting from reactions of the HDL supernate and ten-fold diluted plasma samples with the cholesterol specific and triglycerides specific reagents relative to the absorbance measurements resulting from reactions of the calibrating solution with the cholesterol specific and triglycerides specific reagents. Other constituents present in plasma such as glucose, lactate dehydrogenase (LD/LD-1), albumin, alkaline phosphatase, amylase, bilirubin, urea ((blood/urea/nitrogen) or (BUN), calcium creatinine, aspartate aminotransferase (GOT), hemoglobin, phosphorous, total protein, uric acid, et cetera can be determined according to a similar procedure wherein appropriate light sources 70 are included in the instrument 50 and appropriate reagents and calibrating solutions are included in the doughnut shaped container 10. The concentration of VLDL cholesterol is calculated by dividing the determined triglycerides concentration by five. The concentration of LDL cholesterol is calculated by subtracting the determined HDL cholesterol concentration and the calculated VLDL cholesterol concentration from the determined total cholesterol concentration. The patient's concentration values for total cholesterol, HDL cholesterol, LDL cholesterol, and triglycerides are provided on a computer printout or display to the operator. An interpretation of the data could be provided with the printout wherein a computer program analyzes whether the LDL cholesterol, total cholesterol and triglycerides are over threshold amounts and, if so, notifies the operator of the risk of the patient developing coronary artery disease.

While the invention has been described in terms of its preferred embodiment wherein a disposable, doughnut shaped container has sixteen chambers, each of which contain appropriate reagents, gel, or water for conducting separations and diagnostic tests for the determination of a patient's LDL cholesterol, HDL cholesterol, total cholesterol, and triglycerides concentration levels, those skilled in the art will recognize that invention can be varied within the spirit and scope of the appended claims.

We claim:

1. A multichambered container adapted to be rotated about a longitudinal axis through said container for determining the concentration of plasma constituents, comprising:

a plurality of chambers integrally formed in said container, each of said chambers defined by a plurality of walls, each of said chambers being non-communicable with each other and said chambers being accessible by a pipetter;

a means for separating plasma from a whole blood sample positioned in a first chamber;

a reagent positioned in a second chamber for reacting with a constituent of said plasma separated from said whole blood sample; and windows positioned in a chamber in said multichambered container for allowing optical monitoring of a reaction occurring in said chamber, whereby rotation about said longitudinal axis through said container causes separation of said plasma from said whole blood sample with said means for separating.

2. A multichambered container as recited in claim 1 wherein said reagent reacts with cholesterol.

3. A multichambered container as recited in claim 1 wherein said reagent reacts with triglycerides.

4. A multichambered container as recited in claim 1 wherein said reagent reacts with glucose.

5. A multichambered container as recited in claim 1 wherein said reagent reacts with lactate dehydrogenase.

6. A multichambered container as recited in claim 1 wherein said plurality of walls defining said first chamber comprise an inside wall, an outside wall, and a pair of side walls connected between said inside wall and said outside wall, a space between said side walls being narrower at said outside wall than at said inside wall.

7. A multichambered container as recited in claim 1 wherein said windows are integrally formed with sad walls of said second chamber.

8. A multichambered container adapted to be rotated about a longitudinal axis through said container for determining the concentration of plasma constituents, comprising:
a plurality of chambers integrally formed in said container, each of said chambers defined by a plurality of walls, each of said chambers being non-communicable with each other and said chambers being accessible by a pipetter;
a thixotropic gel positioned in a first chamber for separating plasma from a whole blood sample;
a first reagent positioned in a second chamber for reacting with a first constituent of said plasma separated from said whole blood sample; and
windows positioned in a chamber in said multichambered container for allowing optical monitoring of a reaction occurring in said chamber, whereby rotation about said longitudinal axis through said container causes separation of said plasma from said whole blood sample with said thixotropic gel.

9. A multichambered container as recited in claim 8 wherein said first reagent reacts with cholesterol.

10. A multichambered container as recited in claim 8 wherein said first reagent reacts with triglycerides.

11. A multichambered container as recited in claim 8 wherein said first reagent reacts with glucose.

12. A multichambered container as recited in claim 8 wherein said first reagent reacts with lactate dehydrogenase.

13. A multichambered container as recited in claim 8 wherein said plurality of walls defining said first chamber comprise an inside wall, an outside said inside wall and said outside wall, a space between said side walls being narrower at said outside wall than at said inside wall.

14. A multichambered container as recited in claim 8 wherein said windows are integrally formed with said walls of said second chamber.

15. A multichambered container as recited in claim 8 further comprising a means for separating a high density lipoprotein cholesterol constituent of said plasma separated from said whole blood sample from both a low density lipoprotein cholesterol and a very low density lipoprotein cholesterol constituent of said plasma separated from said whole blood sample positioned in a third chamber.

16. A multichambered container as recited in claim 15 wherein said means for separating said high density lipoprotein cholesterol constituent of said plasma separated from said whole blood sample from both said low density lipoprotein cholesterol and said very low density lipoprotein cholesterol constituents of said plasma separated from said whole blood sample comprises a precipitating reagent which precipitates said low density lipoprotein cholesterol and said very low density lipoprotein cholesterol constituents from said plasma separated from said whole blood sample.

17. A multichambered container as recited in claim 16 wherein said plurality of walls defining said third chamber comprise an inside wall, an outside wall, and a pair of side walls connected between said inside wall and said outside wall, said outside wall including grooves for holding a precipitant thereagainst.

18. A multichambered container as recited in claim 15 further comprising a second reagent positioned in a fourth chamber for reacting with said high density lipoprotein cholesterol constituent of said plasma separated from said whole blood sample.

19. A multichambered container as recited in claim 18 wherein said first reagent reacts with triglycerides.

20. A multichambered container as recited in claim 18 wherein said first reagent reacts with cholesterol.

21. A multichambered container as recited in claim 18 further comprising windows integrally formed with walls defining said fourth chamber.

22. A multichambered container as recited in claim 8 further comprising a second reagent positioned in a third chamber for reacting with a second constituent of said plasma separated from said whole blood sample, said second constituent being different from said first constituent, said third chamber having optical windows positioned in said walls through which a chemical reaction in said third chamber can be monitored.

23. A multichambered container as recited in claim 22 wherein said first reagent reacts with cholesterol and said second reagent reacts with triglycerides.

24. A multichambered container as recited in claim 22 wherein said optical windows in said third chamber are integrally formed with said walls.

25. A multichambered container as recited in claim 8 further comprising a first calibrating solution having a known concentration of said first constituent of said plasma separated from said whole blood sample positioned in a third chamber, a fourth chamber having optical windows positioned in said walls through which a chemical reaction in said fourth chamber can be monitored, and a quantity of said first reagent being positioned in said fourth chamber for reacting with said calibrating solution having said known concentration of said first constituent.

26. A multichambered container as recited in claim 25 wherein said optical windows in said fourth chamber are integrally formed with said walls.

27. A multichambered container as recited in claim 25 wherein said first reagent reacts with triglycerides.

28. A multichambered container as recited in claim 25 wherein said first reagent reacts with cholesterol.

29. A multichambered container as recited in claim 25 comprising a second reagent positioned in a fifth chamber for reacting with a second constituent of said plasma separated from said whole blood sample, said second constituent being different from said first constituent, said fifth chamber having optical windows positioned in said walls through which a chemical reaction in said fifth chamber can be monitored, a second calibrating solution having a known concentration of said second constituent of said plasma separated from said whole blood sample positioned in a sixth chamber, a seventh chamber having optical windows positioned in said walls through which a chemical reaction in said seventh chamber can be monitored, and a quantity of said second reagent being positioned in said seventh chamber for reacting with said calibrating solution having said known concentration of said second constituent.

30. A multichambered container as recited in claim 29 wherein said first reagent reacts with cholesterol and said second reagent reacts with triglycerides.

31. A multichambered container as recited in claim 29 wherein said first and second calibrating solutions are the same and include known concentrations of cholesterol and glycerol.

32. A multichambered container as recited in claim 29 wherein said optical windows in said fifth and seventh chambers are integrally formed with said walls.

33. A multichambered container as recited in claim 8 further comprising a lid affixed to said container, said lid having a plurality of openings providing access to each of said plurality of chambers.

34. A multichambered container as recited in claim 33 further comprising membranes adhered over each of said openings in said lid.

35. A multichambered container as recited in claim 34 wherein each of said membranes are comprised of a rubber coated plastic.

36. A multichambered container as recited in claim 33 wherein said lid is affixed by an ultrasonic weld.

37. An instrument for performing diagnostic tests on a patient's whole blood sample, comprising:
a multichambered container positioned on a spindle comprising a plurality of chambers integrally formed in said container, each of said chambers defined by a plurality of walls, each of said chambers being noncommunicable with each other and said chambers being accessible by a pipetter, a thixotropic gel positioned in a first chamber for separating plasma from a whole blood sample, and a reagent positioned in a second chamber for reacting with a constituent of said plasma separated from said whole blood sample, and windows positioned in a chamber in said multichambered container for allowing optical monitoring of a reaction occurring in said chamber;
a means for rotating said spindle at both high and low speeds;
a pipettor having a needle translatable into and out of at least one of said chambers of said multichambered container, said pipettor capable of retrieving fluid from one of said chambers and dispensing said fluid into another of said chambers;
a monitoring system positioned to monitor said chemical reaction in said second chamber; and
a means for determining a concentration value for said constituent of said plasma separated from said whole blood sample from data output from said monitoring system.

38. An instrument as recited in claim 37 wherein said means for rotating said spindle comprises both high speed and low speed motors, said high speed and low speed motors being alternatively connectable to said spindle for rotating said spindle.

39. An instrument as recited in claim 28 wherein said low speed motor is capable of precisely positioning each of said chambers of said multichambered container on said spindle relative to said pipettor needle, said pipettor needle translatable on a Z-axis.

40. An instrument as recited in claim 37 wherein said monitoring system comprises a light source, a reference detector, and a measurement detector, said measurement detector detecting light which passes through said windows in said chamber having said windows in said container, said reference detector detecting light which does not pass through said windows in said chamber.

41. An instrument as recited in claim 40 wherein said light source is positioned in a hub inside said spindle and said measurement detector is positioned in a chassis, said multichambered container positioned to rotate with said spindle such that said plurality of chambers pass between an optical path between said light source and said measurement detector.

42. A multichambered container adapted to be rotated about a longitudinal axis through said container for determining the concentration of plasma constituents, comprising:
a plurality of chambers integrally formed in said container, each of said chambers defined by a plurality of walls, each of said chambers being non-communicable with each other and said chambers being accessible by a pipetter;
a separation chamber including a means for separating a first constituent from a biological fluid by centrifugation;
a reagent positioned in a reagent chamber for reacting with a second constituent in said biological fluid; and
windows positioned in a chamber in said multichambered container for allowing optical monitoring of a reaction occurring in said chamber, whereby rotation about said longitudinal axis through said container causes separation of said first constituent from said biological fluid.

43. A multichambered container as recited in claim 42 wherein said means for separating in said chamber includes a means for collecting a precipitate on an outward wall under a centrifugal force.

44. A multichambered container as recited in claim 43 wherein said biological fluid is blood plasma and said first constituent is low density lipoprotein cholesterol and said second constituent is high density lipoprotein cholesterol.

45. A multichambered container as recited in claim 42 wherein said windows are integrally formed with the walls of said reagent chamber.

46. A multichambered container as recited in claim 42 further comprising a calibrating solution positioned in a calibrant chamber, said calibrating solution calibrating for said second constituent.

47. A multichambered container as recited in claim 42 further comprising a diluting solution positioned in a diluent chamber.

* * * * *